(12) United States Patent
Boyer, II et al.

(10) Patent No.: US 6,776,800 B2
(45) Date of Patent: Aug. 17, 2004

(54) IMPLANTS FORMED WITH DEMINERALIZED BONE

(75) Inventors: Michael L. Boyer, II, Paoli, PA (US); David C. Paul, Phoenixville, PA (US); Christopher M. Angelucci, Schwenksville, PA (US)

(73) Assignee: Synthes (U.S.A.), Paoli, PA (US)

( * ) Notice: Subject to any disclaimer, the term of this patent is extended or adjusted under 35 U.S.C. 154(b) by 10 days.

(21) Appl. No.: 09/927,334

(22) Filed: Aug. 13, 2001

(65) Prior Publication Data

US 2002/0120338 A1 Aug. 29, 2002

Related U.S. Application Data

(60) Provisional application No. 60/271,745, filed on Feb. 28, 2001.

(51) Int. Cl.[7] ................................................. A61F 2/28
(52) U.S. Cl. ................................. 623/23.63; 623/16.11
(58) Field of Search .......................... 623/17.11, 17.19, 623/23.63, 16.11; 606/70

(56) References Cited

U.S. PATENT DOCUMENTS

| 2,621,145 A | 12/1952 | Sano ............................ 167/84 |
| 4,430,760 A | 2/1984 | Smestad ......................... 3/1.9 |
| 4,627,853 A | 12/1986 | Campbell et al. ............. 623/16 |

(List continued on next page.)

FOREIGN PATENT DOCUMENTS

| DE | 29 10 627 A1 | 9/1980 |
| FR | 2 645 748 | 10/1990 |
| SU | 1465040 A1 | 3/1989 |
| WO | WO 95/21053 | 8/1995 |
| WO | WO 99/38461 | 8/1999 |
| WO | WO 00/07527 | 2/2000 |
| WO | WO 00/07528 | 2/2000 |
| WO | WO 00/30568 | 6/2000 |
| WO | WO 00/40177 | 7/2000 |
| WO | WO 00/40179 | 7/2000 |

OTHER PUBLICATIONS

Kai–Uwe Lewandrowski, "Improvement of Incorporation of Bone Allografts," CRISP grant abstract, Fiscal Year 2000.
Joseph Catanese III et al., "Heterogeneity of the mechanical properties of demineralized bone," *Journal of Biomechanics*, vol. 32, pp. 1365–1369, 1999.
Kai–Uwe Lewandrowski et al., "Mechanical Properties of Perforated and Partially Demineralized Bone Grafts," *Clinical Orthopaedics and Related Research*, No. 353, pp. 238–246, 1998.
Kai–Uwe Lewandrowski et al., "Improved Osteoinduction of Cortical Bone Allografts: A Study of the Effects of Laser Perforation and Partial Demineralization," *Journal of Orthopaedic Research*, vol. 15, pp. 748–756, 1997.

(List continued on next page.)

*Primary Examiner*—Paul B. Prebilic
(74) *Attorney, Agent, or Firm*—Jones Day

(57) ABSTRACT

Selectively partially and demineralized bone-derived implants, their methods of preparation and use are provided. In one embodiment, a cranial void filler preferably having a T-shape formed of an upper mineralized cortical bone section and at least a partially demineralized lower section adapted to fill a cranial void is disclosed. In another embodiment, a plate preferably having a dog-bone-shape having mineralized and at least partially demineralized sections is disclosed. In a further embodiment, a unitary cord having a first mineralized section with a plurality of slits to provide flexibility and a second at least partially demineralized section is described. Also disclosed is an implant for laminoplasty having at least a partially demineralized section and a mineralized section. A method of forming an implant of demineralized fibers also is disclosed.

16 Claims, 14 Drawing Sheets

U.S. PATENT DOCUMENTS

| | | | | |
|---|---|---|---|---|
| 4,717,115 | A | 1/1988 | Schmitz et al. | 249/112 |
| 4,950,295 | A | 8/1990 | Weigum et al. | 623/16 |
| 4,994,084 | A | 2/1991 | Brennan | 623/11 |
| 5,053,049 | A | 10/1991 | Campbell | 623/16 |
| 5,084,051 | A | 1/1992 | Törmälä et al. | 606/77 |
| 5,092,887 | A | 3/1992 | Gendler | 623/13 |
| 5,133,755 | A | 7/1992 | Brekke | 623/16 |
| 5,258,043 | A | 11/1993 | Stone | 623/66 |
| 5,284,655 | A | 2/1994 | Bogdansky et al. | 424/422 |
| 5,298,254 | A | 3/1994 | Prewett et al. | 424/422 |
| 5,306,304 | A | 4/1994 | Gendler | 623/16 |
| 5,314,476 | A | 5/1994 | Prewett et al. | 623/16 |
| 5,329,846 | A | 7/1994 | Bonutti | 100/50 |
| 5,366,508 | A | 11/1994 | Brekke | 623/16 |
| 5,403,317 | A | 4/1995 | Bonutti | 606/80 |
| 5,425,770 | A | 6/1995 | Piez et al. | 623/16 |
| 5,439,684 | A | 8/1995 | Prewett et al. | 424/422 |
| 5,464,439 | A | 11/1995 | Gendler | 623/16 |
| 5,501,706 | A | 3/1996 | Arenberg | 623/16 |
| 5,507,813 | A | 4/1996 | Dowd et al. | 623/16 |
| 5,545,222 | A | 8/1996 | Bonutti | 623/11 |
| 5,556,430 | A | 9/1996 | Gendler | 623/16 |
| 5,569,308 | A | 10/1996 | Sottosanti | 633/165 |
| 5,607,474 | A | 3/1997 | Athanasiou et al. | 623/11 |
| 5,665,120 | A | 9/1997 | Ohtsuka et al. | 623/16 |
| 5,697,981 | A | 12/1997 | Ison et al. | 623/16 |
| 5,725,813 | A | 3/1998 | Nies | 264/15 |
| 5,728,157 | A | 3/1998 | Prescott | 623/11 |
| 5,728,159 | A | 3/1998 | Stroever et al. | 623/16 |
| 5,733,288 | A | 3/1998 | Allen | 606/79 |
| 5,824,078 | A | 10/1998 | Nelson et al. | 623/66 |
| 5,824,084 | A | 10/1998 | Muschler | 623/16 |
| 5,868,749 | A | 2/1999 | Reed | 606/76 |
| 5,876,452 | A | 3/1999 | Athanasiou et al. | 623/16 |
| 5,876,455 | A | 3/1999 | Harwin | 623/16 |
| 5,879,403 | A | 3/1999 | Ostiguy et al. | 623/22 |
| 5,888,219 | A | 3/1999 | Bonutti | 623/11 |
| 5,899,939 | A | 5/1999 | Boyce et al. | 623/16 |
| 5,904,716 | A | 5/1999 | Gendler | 623/11 |
| 5,910,315 | A | 6/1999 | Stevenson et al. | 424/422 |
| 5,958,314 | A | 9/1999 | Draenert | 264/42 |
| 5,968,047 | A | 10/1999 | Reed | 606/76 |
| 5,972,034 | A | 10/1999 | Hofmann et al. | 623/23 |
| 5,981,828 | A | 11/1999 | Nelson et al. | 623/16 |
| 5,997,581 | A | 12/1999 | Khalili | 623/23 |
| 6,013,853 | A | 1/2000 | Athanasiou et al. | 623/11 |
| 6,030,635 | A | 2/2000 | Gertzman et al. | 424/423 |
| 6,045,554 | A | 4/2000 | Grooms et al. | 606/73 |
| 6,049,025 | A | 4/2000 | Stone et al. | 623/16 |
| 6,060,640 | A | 5/2000 | Pauley et al. | 623/11 |
| 6,090,998 | A | 7/2000 | Grooms et al. | 623/16 |
| 6,110,482 | A | 8/2000 | Khouri et al. | 424/423 |
| 6,123,731 | A | 9/2000 | Boyce et al. | 623/23.63 |
| 6,143,030 | A | 11/2000 | Schroder | 623/16.11 |
| 6,200,347 | B1 | 3/2001 | Anderson et al. | 623/16.11 |
| 6,206,923 | B1 * | 3/2001 | Boyd et al. | 623/17.11 |
| 6,277,397 | B1 | 8/2001 | Shimizu | 424/443 |
| 6,432,436 | B1 | 8/2002 | Gertzman et al. | 424/423 |
| 6,436,138 | B1 | 8/2002 | Dowd et al. | 623/16.11 |
| 6,440,444 | B2 | 8/2002 | Boyce et al. | 424/422 |
| 6,458,158 | B1 | 10/2002 | Anderson et al. | 623/16.11 |
| 6,458,162 | B1 | 10/2002 | Koblish et al. | 623/23.51 |
| 2001/0010021 | A1 | 7/2001 | Boyd et al. | 623/17.13 |
| 2001/0014667 | A1 | 8/2001 | Chen et al. | 514/12 |
| 2001/0014831 | A1 | 8/2001 | Scarborough | 623/23.51 |
| 2002/0081959 | A1 | 6/2002 | Benedict et al. | 452/198 |
| 2002/0091447 | A1 | 7/2002 | Shimp et al. | 623/17.16 |
| 2002/0106393 | A1 | 8/2002 | Bianchi et al. | 424/423 |
| 2002/0107570 | A1 | 8/2002 | Sybert et al. | 623/13.17 |
| 2002/0107571 | A1 | 8/2002 | Foley | 623/17.11 |

OTHER PUBLICATIONS

Kai–Uwe Lewandroski et al., "Kinetics of cortical bone demineralization: Controlled demineralization—a new method for modifying cortical bone allografts," *Journal of Biomedical Materials Research*, vol. 31, pp. 365–372, 1996.

Douglas W. Jackson et al., "Biologic Remodeling after Anterior Cruciate Ligament Reconstruction Using a Collagen Matrix Derived from Demineralized Bone," *American Journal of Sports Medicine*, vol. 24, pp. 405 414, 1996.

Kai–Uwe Lewandrowski et al., "Flexural Rigidity in Partially Demineralized Diaphyseal Bone Grafts," *Clinica Orthopaedics and Related Research*, No. 317, pp. 254–262, 1995.

J.J. Broz et al., "Material and Compositional Properties of Selectively Demineralized Cortical Bone," *J. Biomechanics*, vol. 28, pp. 1357–1368, 1995.

Howard S. An et al., "Comparison Between Allograft Plus Demineralized Bone Matrix Versus Autograft in Anterior Cervical Fusion. A Prospective Multicenter Study," *Spine*, vol. 20, pp. 2211–2216, 1995.

Norbert Kübler et al., "Osteoinductive, Morphologic, and Biomechanical Properties of Autolyzed, Antigen–Extracted, Allogeneic Human Bone," *J. Oral Maxillofac. Surg.*, vol. 51, pp. 1346–1357, 1993.

S. M. Tuli et al., "The Osteoinductive Property of Decalcified Bone Matrix. An Experimental Study," *The Journal of Bone and Joint Surgery*, vol. 60–B, pp. 116–123, 1978.

Marshall R. Urist, "Surface–Decalcified Allogeneic Bone (SDAB) Implants. A Preliminary Report of 10 Cases and 25 Comparable Operations With Undecalcified Lyophilized Bone Implants.," *Clinical Orthopaedics and Related Research*, No. 56, pp. 37–50, 1968.

Fred H. Albee, *Bone Graft Surgery in Disease, Injury and Deformity*, D. Appleton–Century Company, Inc., New York, 1940, pp. 30, 65–67, 114, 151, 155, 164, 212, 256–257, 270–273, 311–313.

Fred H. Albee, "Bone Surgery With Machine Tools," *Scientific American*, Apr., 1936, pp. 178–181.

Fred H. Albee, *Bone–Graft Surgery*, W. B. Saunders Company, Philadelphia, Pennsylvania, 1915, pp. 90–92, 145, 165–166, 171, 368–369.

* cited by examiner

IMPLANTS FORMED WITH DEMINERALIZED BONE

CROSS-REFERENCE TO RELATED APPLICATIONS

The benefit of Provisional Application No. 60/271,745 filed Feb. 28, 2001 is claimed under 35 U.S.C. § 119(e).

FIELD OF THE INVENTION

The invention is related to implants formed from bone. More particularly, the invention is related to implants formed from partially demineralized or demineralized bone.

BACKGROUND OF THE INVENTION

Bone grafts have become an important and accepted means for treating bone fractures and defects. In the United States alone, approximately half a million bone grafting procedures are performed annually, directed to a diverse array of medical interventions for complications such as fractures involving bone loss, injuries or other conditions necessitating immobilization by fusion (such as for the spine or joints), and other bone defects that may be present due to trauma, infection, or disease. Bone grafting involves the surgical transplantation of pieces of bone within the body, and generally is effectuated through the use of graft material acquired from a human source. This is primarily due to the limited applicability of xenografts, transplants from another species.

Orthopedic autografts or autogenous grafts involve source bone acquired from the same individual that will receive the transplantation. Thus, this type of transplant moves bony material from one location in a body to another location in the same body, and has the advantage of producing minimal immunological complications. It is not always possible or even desirable to use an autograft. The acquisition of bone material from the body of a patient typically requires a separate operation from the implantation procedure. Furthermore, the removal of material, oftentimes involving the use of healthy material from the pelvic area or ribs, has the tendency to result in additional patient discomfort during rehabilitation, particularly at the location of the material removal. Grafts formed from synthetic material have also been developed, but the difficulty in mimicking the properties of bone limits the efficacy of these implants.

As a result of the challenges posed by autografts and synthetic grafts, many orthopedic procedures alternatively involve the use of allografts, which are bone grafts from other human sources (normally cadavers). The bone grafts, for example, are placed in a host bone and serve as the substructure for supporting new bone tissue growth from the host bone. The grafts are sculpted to assume a shape that is appropriate for insertion at the fracture or defect area, and often require fixation to that area as by screws or pins. Due to the availability of allograft source material, and the widespread acceptance of this material in the medical community, the use of allograft tissues is certain to expand in the field of musculoskeletal surgery.

With respect to the overall structure of a given bone, the mechanical properties vary throughout the bone. For example, a long bone (leg bone) such as the femur has both compact bone and spongy bone. Cortical bone, the compact and dense bone that surrounds the marrow cavity, is generally solid and thus carries the majority of the load in major bones. Cancellous bone, the spongy inner bone, is generally porous and ductile, and when compared to cortical bone is only about one-third to one-quarter as dense, one-tenth to one-twentieth as stiff, but five times as ductile. While cancellous bone has a tensile strength of about 10–20 MPa and a density of about 0.7, cortical bone has a tensile strength of about 100–200 MPa and a density of about 2. Additionally, the strain to failure of cancellous bone is about 5–7%, while cortical bone can only withstand 1–3% strain before failure. It should also be noted that these mechanical characteristics may degrade as a result of numerous factors such as any chemical treatment applied to the bone material, and the manner of storage after removal but prior to implantation (i.e. drying of the bone). In addition, bones have a grain direction similar to the grain found in wood, and thus the strength of the bone varies depending on the orientation of the grain.

Notably, implants of cancellous bone incorporate more readily with the surrounding host bone, due to the superior osteoconductive nature of cancellous bone as compared to cortical bone. Furthermore, cancellous bone from different regions of the body is known to have a range of porosities. For example, cancellous bone in the iliac crest has a different porosity from cancellous bone in a femoral head. Thus, the design of an implant using cancellous bone may be tailored to specifically incorporate material of a desired porosity.

Demineralization of cortical, cancellous, and corticocancellous bone of autograft, allograft, and xenograft types is known. In one form, bone powder or chips are chemically processed using an acid such as hydrochloric acid, chelating agents, electrolysis or other treatments. The demineralization treatment removes the minerals contained in the natural bone, leaving collagen fibers with bone growth factors including bone morphogenic protein (BMP).

The use of expandable materials as a prosthetic element is disclosed in U.S. Pat. No. 5,545,222 to Bonutti. Materials disclosed which expand when they come in contact with water or other fluids include PEEK (polyether-etherketone), a desiccated biodegradable material, or a desiccated allograft. As an example, a tendon can be compressed in a desiccated state, and as it imbibes water it expands and creates a firmer lock or tighter fit in the host site.

A shaped, swollen demineralized bone and its use in bone repair is disclosed in U.S. Pat. No. 5,298,254 to Prewett et al. In general, cortical allogeneic bone tissue is preferred as the source of bone. Demineralized bone is contacted with a biocompatible swelling agent for a period of time sufficient to cause swelling of the piece.

A flexible implant using partially demineralized bone is disclosed in U.S. Pat. No. 6,206,923 to Boyd et al. The bone implant has a first substantially rigid portion and a second substantially rigid portion which are joined by an intermediate portion that has been at least partially demineralized to create an area of flexibility in the bone implant. The pair of rigid bone portions cooperate to provide support for spacing between adjacent vertebra.

Demineralized bone has been disclosed for use as artificial ligaments in U.S. Pat. No. 5,092,887 to Gendler. Completely or partially demineralized cortical bone is sliced in strips and rods of approximately 0.1–1.5 centimeters wide and 0.1–1.5 centimeters thick with compliant elasticity and longitudinal strength similar to natural ligaments and tendons. The strips or rods are used as artificial ligaments for in vivo replacement, repair and augmentation of damaged ligaments, tendons or other fibrous tissue that permanently connects first and second body members such as the femur and tibia. Disclosure of a segmentally demineralized bone implant is found in U.S. Pat. No. 6,090,998 to Grooms et al.

The implant comprises a first mineralized portion or segment, and a second, flexible, demineralized portion or segment that are produced by machining a piece of cortical bone.

A textured, demineralized, and unitary mammalian bone section for providing a rigid, foraminous, collagen scaffold for allogenic skeletal reconstruction is disclosed in U.S. Pat. No. 5,112,354 to Sires. Texturing or pore formation is carried out prior to demineralization to permit completeness of demineralization and additionally promote osteoinduction due to the increased surface area. Pores of between 200 μm and 2000 μm are created with a laser. The depth of the holes in the bone may be varied.

Also disclosed in U.S. Pat. No. 5,899,939 to Boyce et al. is a bone-derived implant for load-supporting applications. The implant is formed of one or more layers of fully mineralized or partially demineralized cortical bone and, optionally, one or more layers of some other material such as fully demineralized bone or mineral substances such as hydroxyapatite. The layers constituting the implant are assembled into a unitary structure to provide an implant with load-supporting properties. Superimposed layers are assembled into a unitary structure such as with biologically compatible adhesives.

U.S. Pat. No. 5,556,430 discloses flexible membranes produced from organic bone matrix for skeletal repair and reconstruction. Completely or partially demineralized organic bone is sliced into thin sheets. The bone may be perforated prior to demineralization, to increase the osteoinductivity of the final bone product. Similarly, U.S. Pat. No. 5,298,254 to Prewett et al. discloses demineralized bone sliced into a thin sheet which can be used to patch an injury.

A cortical bone interference screw is disclosed in U.S. Pat. No. 6,045,554 to Grooms et al. The interference screw has a cortical surface into which a self-tapping thread is machined.

In addition, U.S. Pat. No. 5,053,049 to Campbell discloses the use of milling, grinding, and pulverizing to produce pulverized bone with the desired particle size. The pulverized bone can then be combined with any suitable biologically compatible or inert carrier substance, which should have a consistency that imparts the desired flexible texture to the pulverized bone/carrier suspension, or should solidify to the desired consistency after molding or casting.

Despite these developments, there exists a need for implants formed from partially or fully demineralized cancellous bone. Furthermore, there exists a need for implants formed of bone that have been selectively masked during demineralization so that portions of the bone are at least partially demineralized while other portions are substantially remain in the mineralized state.

SUMMARY OF THE INVENTION

According to one embodiment, a cranial void filler is described herein and comprises an upper mineralized cortical bone section, and a lower, at least partially demineralized cortical bone section, wherein the lower section is adapted and configured to contact walls of a cranial void. Preferably, the upper and lower sections form a T-shape. One or more slits may extend through the upper or lower sections, or both, or portions thereof. The slits in the lower section may be colinear with the slits in the upper section. The upper section may have a rounded upper surface portion and also may have a curved lower surface portion.

According to another embodiment, a plate is described. The plate of this embodiment comprises a unitary body formed of cortical bone with a pair of portions having a first width and a central portion disposed therebetween having a second width, the first width being greater than the second width, and the body having at least one partially demineralized region wherein the at least one partially demineralized region provides flexibility to the plate. The plate further may comprise a plurality of fastener holes. The body may have a central longitudinal axis and a first at least partially demineralized region that is coaxial therewith. The first at least partially demineralized region may extend substantially across the entire length of the body. The fastener holes may be disposed proximate the ends of the body. The fastener holes may be disposed on a central longitudinal axis, and a first at least partially demineralized region may be coaxial therewith. One or more second at least partially demineralized regions may be disposed transverse to the first at least partially demineralized region. The one or more second at least partially demineralized regions may be generally perpendicular to the first at least partially demineralized region. The one or more second at least partially demineralized regions may intersect one or more fastener holes. The body may be relatively thin compared to its length or width. The at least partially demineralized region may extend substantially across the second width. The body may have a central longitudinal axis and the at least partially demineralized region may extend transverse to the central longitudinal axis.

The plate may further comprise a plurality of fastener holes and the body may be generally dog-bone-shaped. The body may have a central longitudinal axis, and the length of the body along the central axis may be between about 10 mm and about 20 mm. The first width may be between about 4 mm and about 7 mm and the body may have a thickness between about 1 mm and about 3 mm. The body may have a length of about 15 mm, a first width of about 5 mm, and a thickness of about 2 mm.

In a further embodiment, an implant comprising a unitary section of cortical bone having a first portion that is mineralized and a second portion that is at least partially demineralized, wherein the mineralized portion includes a plurality of slits to facilitate bending of the unitary section is described.

A method of forming an implant also is described. The method comprises the steps of obtaining cortical fibers; at least partially demineralizing the fibers; allowing the fibers to clump together; and allowing the fibers to dry in a clumped state. The fibers may be allowed to dry in a mold and may be pressed while they are clumped together. The fibers may be obtained by milling or other processes.

A still further embodiment describes an implant for maintaining a space in a bisected vertebrae. The implant according to this embodiment comprises a cortical bone cord having first and second free ends adapted for engaging exposed portions of the lamina, and a region positioned between the first and second ends, wherein the region is at least partially demineralized to provide flexibility. The free ends may be mineralized. The cord may comprise a pair of at least partially demineralized regions with a mineralized region therebetween. The at least partially demineralized region may be centrally located between mineralized free ends.

BRIEF DESCRIPTION OF THE DRAWINGS

Preferred features of the present invention are disclosed in the accompanying drawings, wherein.

DETAILED DESCRIPTION OF THE PREFERRED EMBODIMENT

The present invention in one embodiment is directed to an implantable bone sheet that exhibits semi-pliable properties over portions of the sheet, while exhibiting semi-rigid properties over other portions. The variation in properties is achieved by the selective demineralization of bone preferably selected from a femur, tibia, humerus, fibula, ulna, and radius. The terms "demineralization," "demineralized" and "at least partially demineralized" as used herein are intended to refer to fully demineralized bone or partially demineralized bone. The term "fully demineralized" refers to bone where the minerals have been substantially completely removed from the bone whereas the term "partially demineralized" refers to bone where at least some portion of the minerals have been removed. As will become apparent, the degree of demineralization will depend upon the characteristics sought to be achieved in the implant.

Figure 1:
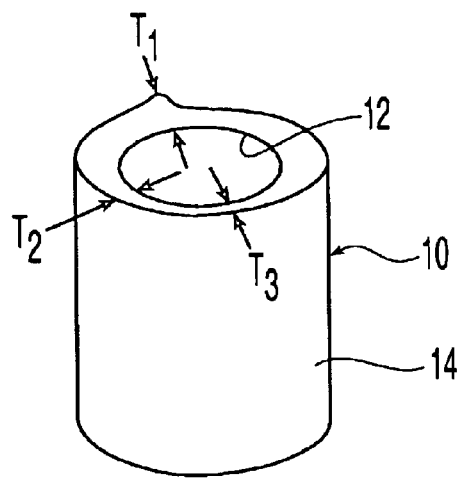
FIG. 1 shows a bone section of a femur.
Figure 2:
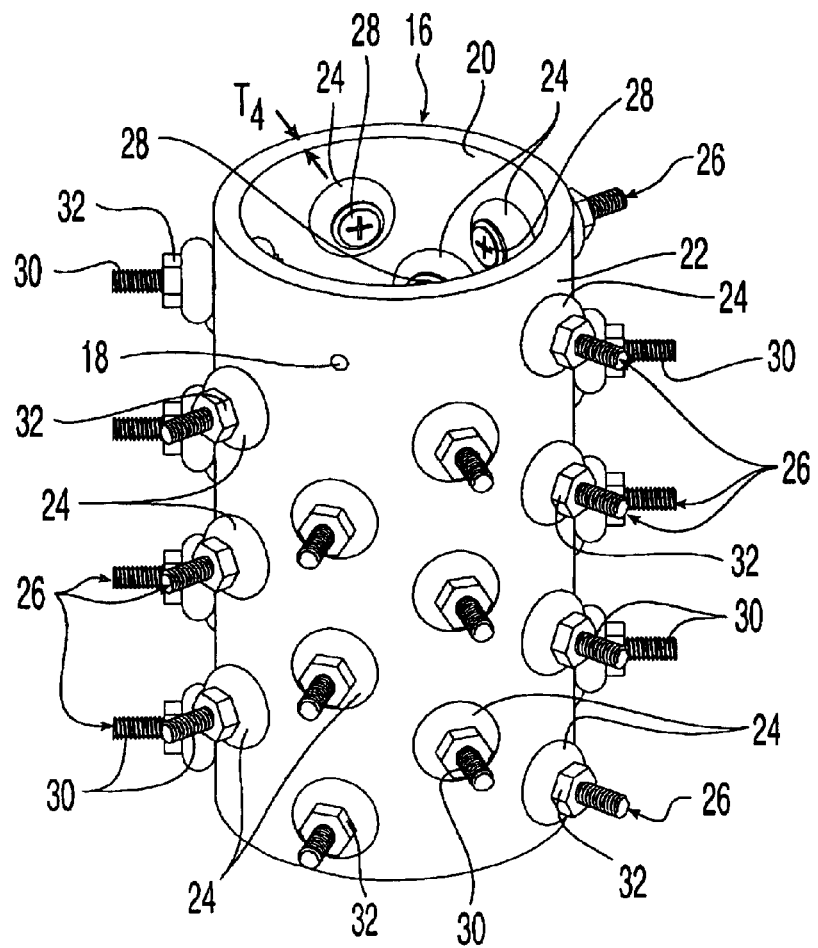
FIGS. 2–3 show a cortical shell of the present invention.

Turning to FIG. 1, a bone section 10 of a femur has an inner surface 12, and an outer surface 14 which initially conforms to the natural shape of the bone. The wall thickness of bone section 10 varies, as indicated by thicknesses $T_1$, $T_2$, and $T_3$. As shown in FIG. 2, bone section 10 may be machined to have a relatively uniform wall thickness $T_4$, forming a cortical shell 16. Initially, cortical shell 16 is generally rigid, and holes 18 are formed from machined inner surface 20 to machined outer surface 22. Holes 18 may be provided in repeating patterns, or as desired.

Figure 3:
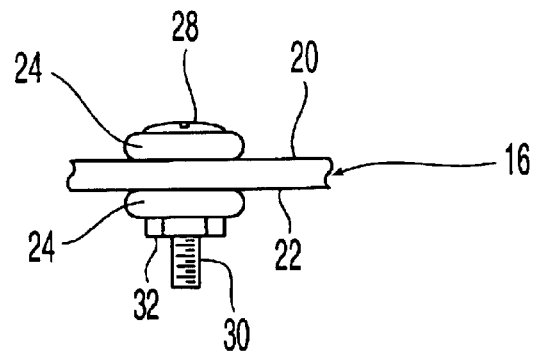

In order to selectively screen areas of cortical shell 16 from direct contact with treatments such as hydrochloric acid, chelating agents, electrolysis, or other suitable treatments, a pair of masking elements 24 are disposed proximate each hole 18, with one masking element 24 disposed on machined inner surface 20 and the other disposed on machined outer surface 22. When tightly retained against surfaces 20, 22, masking elements 24 seal portions of cortical shell 16 from surrounding treatment fluids and reactions. In one preferred embodiment, masking elements 24 are toroidal in shape and have some flexibility such that the toroidal shape may be compressed to bear against the surface of cortical shell 16. Suitable masking elements include rubbery washers, o-rings, and grommets, which preferably have resistance to chemical attack from the treatments to which cortical shell 16 will be subjected. In order to create a secure seal, masking elements 24 are retained in place, using screws 26, the heads 28 of which bear against one masking element 24 and the threaded shafts 30 of which extend through the aligned pair of masking elements 24 and hole 18. Preferably, the screws are formed of a material that does not react with or otherwise contaminate cortical shell 16, such as a suitable polymer. Pressure is applied to masking elements 24 by threadably receiving a nut 32 on each threaded shaft 30 to bear against the other of the masking elements 24 in each pair that is not in contact with a head 28 of screw 26. A partial side view of a pair of masking elements 24 retained against cortical shell 16 are shown in FIG. 3. Although heads 28 of screws 26 are shown disposed inside cortical shell 16 adjacent machined inner surface 20 and nuts 32 are shown disposed outside cortical shell 16 adjacent machined outer surface 22, the reverse configuration is also contemplated.

Other masking elements 24 are also suitable for the present invention. For example, press-fit elastic rings with outer circumferential grooves may be used to seal the regions of cortical shell 16 around each hole 18, as long as adequate surface contact and/or pressure can be applied by the rings to prevent leakage of treatment liquids therebetween. Alternatively, tapes or paints may be applied to serve as masking elements 24 to seal particular regions. For example, an air dry synthetic rubber coating may be used by dipping or otherwise painting select regions of an implant to mask the regions from treatment. Preferably, the aforementioned masking techniques are not only resistant to the bone treatments, but are readily removed following treatment.

Various configurations of masking elements 24 can be chosen to provide the desired amount of protection from treatments. As will now be explained, the present configuration is useful for providing limited regions of mineralized bone surrounded by a field of demineralized bone. Such a configuration is particularly useful, for example, in permitting the production of a generally flexible sheet of demineralized cortical bone with mineralized, rigid regions bordering holes for use in receiving fasteners. Thus, surgical procedures necessitating the attachment of demineralized cortical bone for eventual assimilation into neighboring tissue may make use of a flexible sheet of the present invention that includes regions, for example, for receiving bone screws, with the regions being resistant to tearing or other damage during installation and stressing of the bone sheet.

Figure 4:
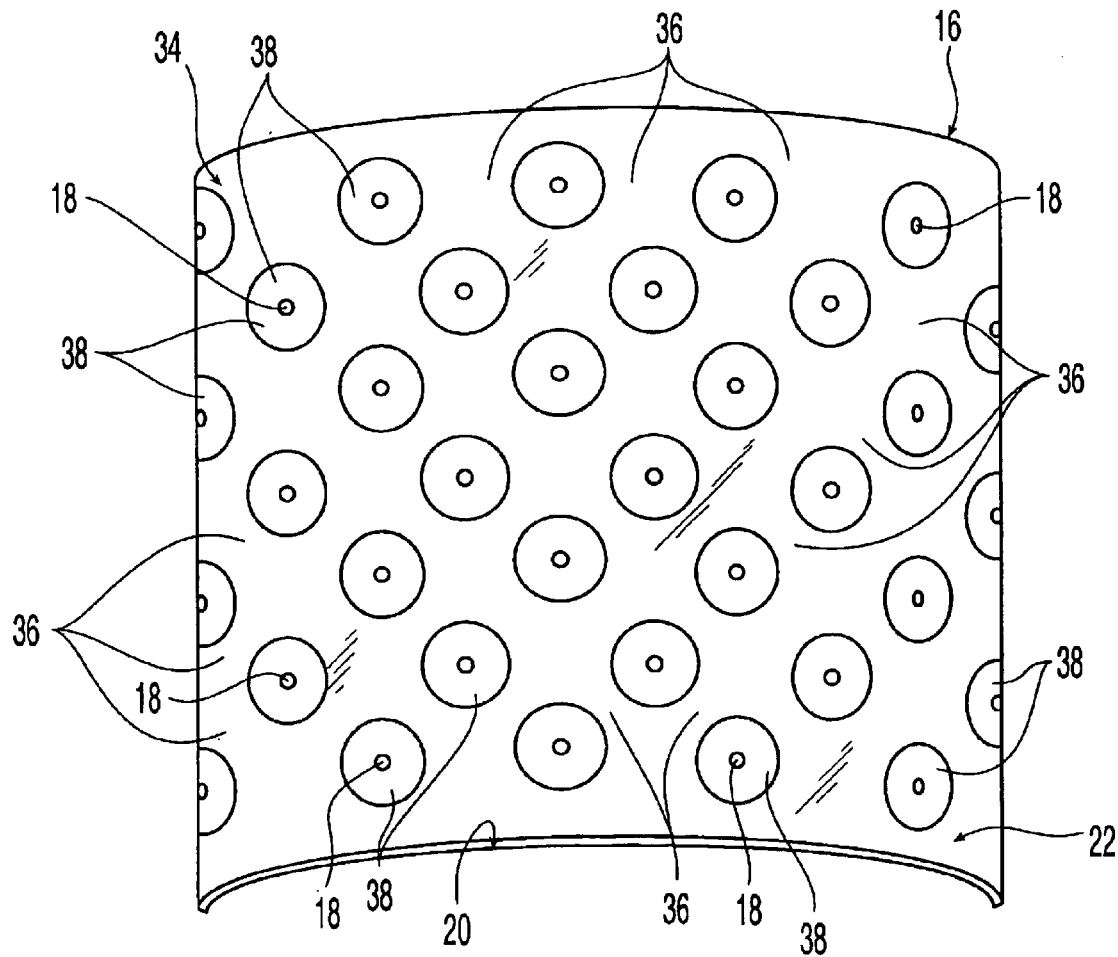
FIG. 4 shows a cortical sheet formed from the cortical shell of FIG. 2.

After suitable masking procedures have been completed, cortical shell 16 is immersed or otherwise treated with a demineralizing agent. While the untreated cortical shell 16 initially possessed rigid properties, the selectively demineralized cortical shell 16 exhibits rubbery, elastic-like properties. Turning to FIG. 4, the treated cortical shell 16 has been cut across its length, such that a sheet 34 is formed. Sheet 34 includes a demineralized field 36 surrounding mineralized regions 38 which are disposed about holes 18. Although not shown, a near mirror image is present on both surfaces 20, 22, and generally extends across the thickness of sheet 34.

Because the selectively demineralized cortical sheet is malleable, and thus generally can be made to conform to the shape of a given anatomical region, such a cortical sheet may also find use in orthopaedic procedures as a "wrapping" material to surround areas requiring surgical intervention, or as a sealing material over defect areas such as regions excised due to tumors. In one embodiment, the cortical sheet may be used as a bridging agent for a bad fracture, and in another embodiment it may be used to encapsulate bone inside a barrier to retain blood and other products in a localized area. Furthermore, the sheet may serve as a patch, such as to cover regions of the skull temporarily removed to permit surgical access to the cranial area. Also, if the sheet is perforated sufficiently, it may serve as a mesh. Preferably, the perforations are substantially smaller than fastener holes provided in the sheet. In addition, the demineralized cortical sheet may be used to surround an iliac crest harvest, instead of the polymer sheet otherwise used. Preferably, the cortical sheet has a thickness of between about 0.5 mm and about 3 mm.

Notably, the above selective demineralization process may be used with bone portions already in sheet-like form prior to selective demineralization treatment. For example, strips of cortical bone may be precut from bone section 10, with holes 18 drilled accordingly. In the case of a cortical shell 16 as discussed above, however, the shell-like structure is preferably kept intact until after treatment due to its rigid and thus fracture-prone characteristics. Although the application of masking elements 24 is more complicated with a shell geometry than with a sheet or strip geometry, the production of selectively demineralized sheets of significantly greater area is possible with the shell-like structures.

Figure 4A:
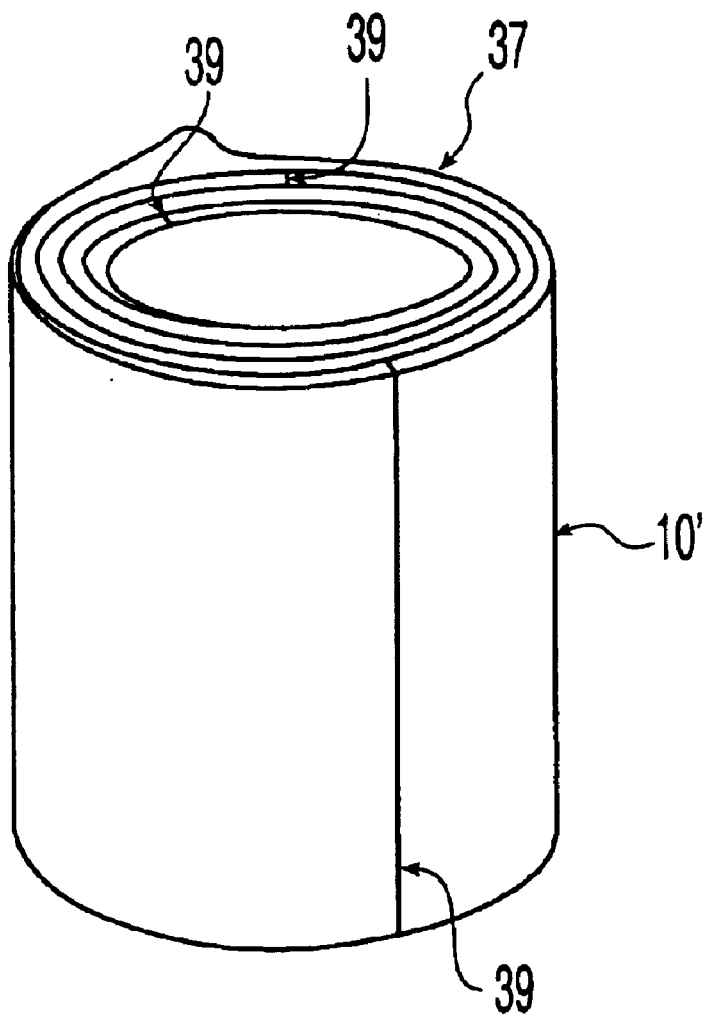
FIG. 4A shows a spiral cortical sheet formed from the cortical shell of FIG. 2.

In an alternate embodiment shown in FIG. 4A, a bone section 10' may be cut in spiral form 37 so that the overall outer and inner geometry of the bone need not be extensively machined to achieve a uniform wall thickness. Longitudinal cuts 39 also may be made such that individual sheets may be produced from the spiral. The cuts can be formed at regular distances through the spiral form 37 so that sheets of desired sizes can be produced. Thus, demineralized or partially demineralized sheets may be formed using this technique.

Figure 4B:
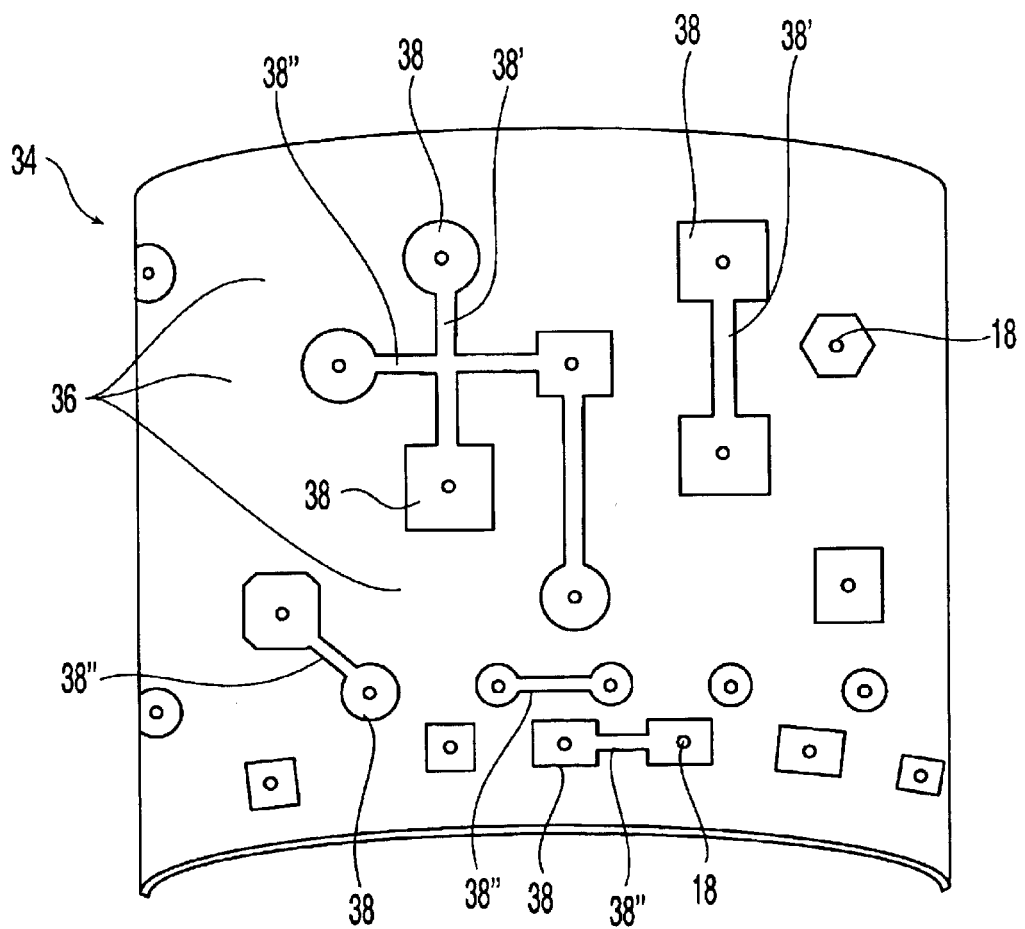
FIG. 4B shows a cortical sheet according to an alternative embodiment.
Figure 5:
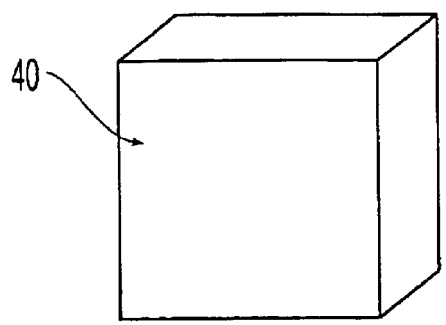
FIGS. 5–7 show various forms of cancellous bone of the present invention.
Figure 6:
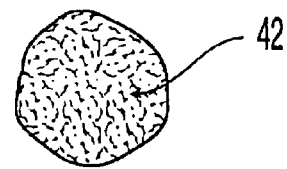
Figure 7:
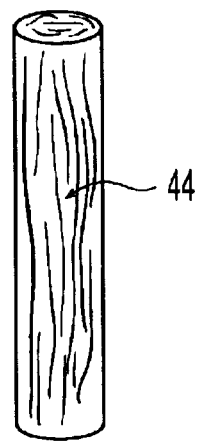
Figure 8:
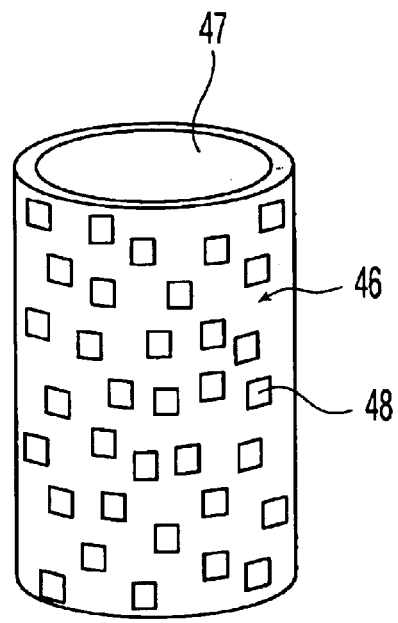
FIG. 8 shows a cage for filling with cancellous bone of FIG. 7.

The mineralized regions 38 which are formed in the demineralized field 36 of sheet 34 may have a configuration other than shown in FIG. 4. For example, mineralized regions 38 may be larger or smaller than shown and may have a different configuration as shown in FIG. 4B. In addition, mineralized regions 38 may be connected together for example by a connecting strip or strut 38' of mineralized bone. The struts 38' may be configured to be directed substantially along parallel axis to provide the sheet with different characteristics in different directions. In this manner, the connecting struts may provide the sheet with a preferred orientation. Struts 38" also may be provided and may be oriented in an orthogonal or other direction from strut 38' to provide the desired properties for sheet 34 in the direction of strut 38". By changing the shape and size of mineralized regions 38 and struts 38' and 38", a sheet having desired directional properties may be designed.

The present invention is also directed to selectively demineralized cancellous bone for filling voids, bone defects, or other regions such as the cavities inside spinal cages. While mineralized cancellous bone may function in some load bearing capacity in wet and dry conditions, demineralized cancellous bone acts like a sponge when it is wet and exhibits "memory" properties when dried and subsequently rehydrated. For example, turning to FIGS. 5–9, a block 40 of cancellous bone may initially be provided in a demineralized state, with an initial geometry and volume $V_1$. Block 40 may be submersed in water, and permitted to assume a soft, hydrated state in which it may be compressed to a smaller configuration such as pellet 42 with new volume $V_2 < V_1$. The compressed pellet 42 is then allowed to dry, and it hardens in the pellet-like configuration instead of the block-like configuration. It should also be noted the when demineralized bone dries, it further shrinks, but it will re-expand when rehydrated. To regain the block-like configuration of block 40, pellet 42 is subsequently rehydrated and permitted to expand back to its original shape and regain soft, spongy properties. Because of this "memory" effect, the demineralized, cancellous bone may be supplied in standard geometries that can be used to fill correspondingly sized cavities, or in geometries that are used to expand and fill any given shape smaller than or equal to their expanded size. In addition, the degree of expansion from compression (i.e., as a function of the volume of void to be filled) may be used to produce a demineralized cancellous body with particular porosity. Swelling agents other than or in addition to water may also be employed.

Figure 9:
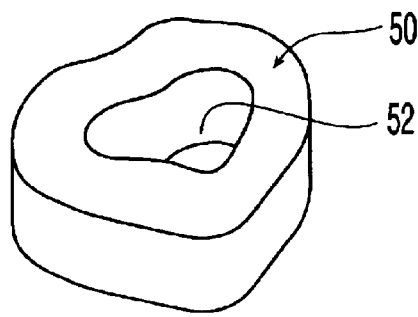
FIG. 9 shows a femur section for filling with demineralized cancellous bone of FIG. 6.
Figure 9A:
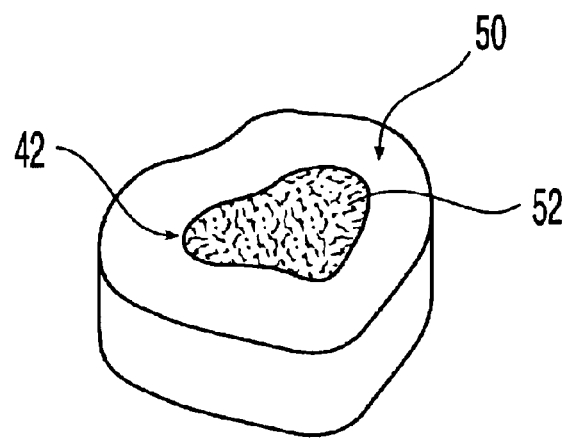
FIG. 9A shows a femur section filled with demineralized cancellous bone of FIG. 6.

In one embodiment, a bone section such as femur section 50 shown in FIG. 9 with an internal channel 52 may be loaded with a pellet 42, and when the pellet 42 is permitted to rehydrate, pellet 42 expands to fill the channel 52 as shown in FIG. 9A. This is particularly useful for irregularly shaped volumes as shown with channel 52.

Figure 8A:
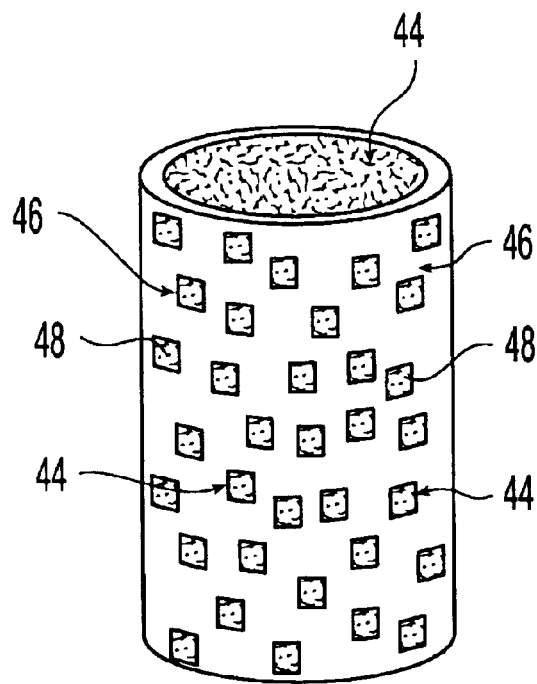
FIG. 8A shows a cage filled with cancellous bone of FIG. 7.

In another embodiment, block 40 may also be compressed to a cylindrical configuration such as a cylinder 44. Cylinder 44 is particularly well adapted for use with a hollow cage 46 with internal cavity 47 and perforations 48, shown in FIG. 8. When a suitably sized cylinder 44 is placed within cage 46 and rehydrated, cylinder 44 expands to fill internal cavity 47 and perforations 48 as shown in FIG. 8A. The cage 46 may or may not be provided with perforations 48 but expansion of the pellet 42 or cylinder 44 or other dried cancellous bone section in perforations 48 helps to retain the bone section within the cage or shell.

In yet another embodiment, a pellet 42 or cylinder 44 may be delivered to a defect region in the body, and rehydrated to fill the defect. Other geometries and degrees of compression are contemplated as well, including a flat, pancake-like configuration, a donut-like configuration, and a dumbell configuration which may be used to expand within a defect such as a through-hole and plug either end of the through-hole. Based on the degree of compression, as well as the degree of demineralization, control of the degree of porosity of the demineralized cancellous bone insert may be achieved.

Figure 10:
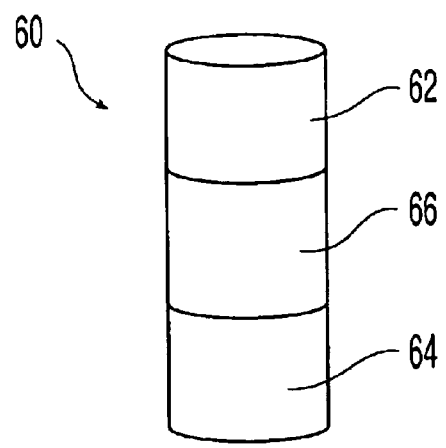
FIG. 10 shows a partially demineralized cancellous bone cylinder of the present invention.

With reference to FIG. 10, a partially demineralized cancellous bone cylinder 60 is shown. Cylinder 60 includes mineralized, rigid portions 62, 64 and a demineralized, sponge-like section 66 therebetween. As discussed above with respect to selectively screening areas of a bone portion from direct contact with chemical treatments, portions 62, 64 are preferably masked during treatment of cylinder 60. In addition, while section 66 is exposed to demineralization treatment, the degree of demineralization can be controlled as a function of the duration of treatment (i.e., submersion time in demineralizing agent) and the strength of the treatment medium (i.e., dilute or strong acid). Thus, the degree of "sponginess" or resiliency may be selected to meet a particular clinical application. Fully or partially demineralized cylinders such as cylinder 60 may be used, for example, to fill bony defects caused by the removal of bone screws during subsequent surgical procedures, to fill bony defects resulting from the removal of diseased bone, or as burr hole covers necessitated by cranial surgery.

Figure 11:
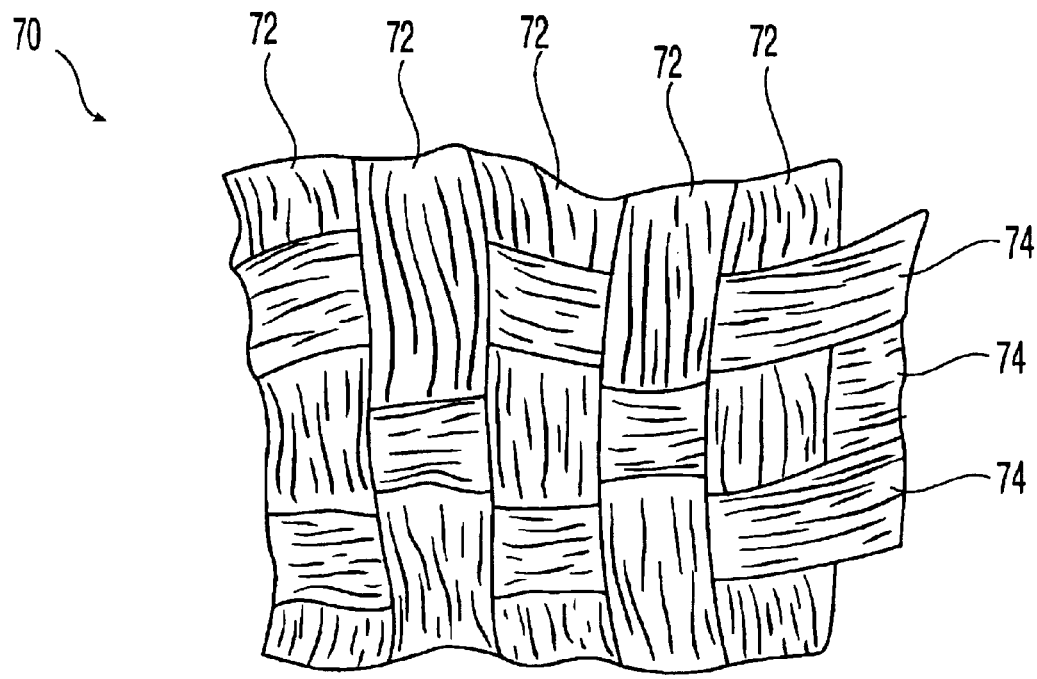
FIG. 11 shows a woven bone implant of the present invention.

Turning again to demineralized cortical bone, the ligament-like, pliable properties of the bone resulting from the demineralization treatment advantageously may be used. Because the properties of bone vary as a function of direction with respect to the bone grains, sheets of pliable bone may be woven together from strips of bone cut at particular orientations with respect to the grains. Woven bone implant 70 is shown in FIG. 11. Strips 72 running generally parallel to each other along a first direction form columns which are woven together with strips 74 that are running generally parallel to each other along a second grain direction forming rows. By disposing the strips in this manner, the properties of woven bone implant advantageously may be tailored to a particular need, for example through the selective orientation of the grains of criss-crossing bone strips. In some embodiments, strips 72, 74 of woven bone implant 70 may each be mineralized, demineralized, or partially demineralized. Also, each strip 72, 74 may include mineralized regions and demineralized regions. The orientation of the grain direction of each of the strips may further be used to tailor the properties of the woven bone implant 70.

As an illustrative, non-limiting example, bone strips 72, 74 may have an overall length less than or equal to the maximum length of a bone from which the strips are produced. Thus, bone strips 72, 74, for example, may be 12 inches in length if a bone has such an overall length. Moreover, the bone strips 72 may be much shorter than an overall bone length, and thus, for example one-inch bone strips 72 may be used. Bone strips 72, 74 may have a width of between about 1 mm and about 6 mm, and a thickness of between about 0.5 mm and about 2 mm. In another embodiment, bone strips 72, 74 may have a width of about 5 mm and a thickness of about 1 mm. The bone strips 72, 74 may be woven in a similar fashion to a basket, as shown for example in FIG. 11. The resulting sheets may have the same uses and applications, for example, as the sheet described in FIG. 4.

In another exemplary embodiment, bone strips preferably at least about 1 mm in thickness and width may be braided, similar to carbon fiber, in uni-directional, bi-directional, two-dimensional, and three-dimensional braid configurations. In yet another exemplary embodiment, individual bone fiber strands, preferably with a thickness of less than about 0.5 mm, may be braided and/or woven to create a bone cloth. An increase in strength may be realized by alternating grain directions, thereby also permitting larger overall implants to be produced. Braids additionally may incorporate other materials, such as laminations, bonding agents, and/or bone inducing substances.

Figure 12:
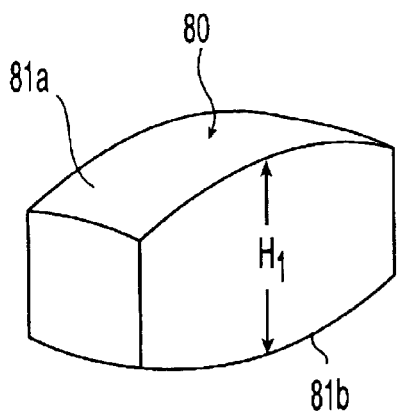
FIG. 12 shows a demineralized cortical bone implant for nucleus replacement according to the present invention.
Figure 12:
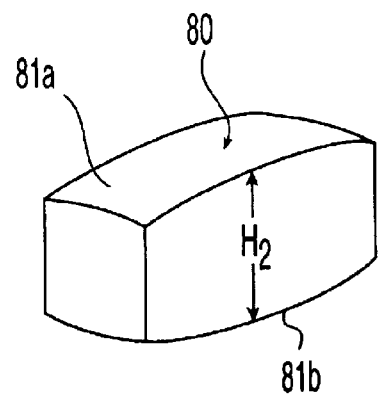

Demineralized bone may also be used in nucleus replacement. The nucleus pulposus is the inner gel-like portion of an intervertebral disc consisting of proteoglycans and a collagen meshwork. Younger individuals possess water in this region, but older individuals lose water resulting in disc degeneration and deydration. Such difficulties are commonly known as disc herniation—the nucleus pulposus herniates through the annulus when this occurs. In one preferred embodiment, as shown in FIG. 12, a demineralized cortical bone implant 80 having an initial height $H_1$ is freeze-dried so that it shrinks to a second height $H_2$, with $H_1 > H_2$. In the smaller configuration, implant 80 is loosely inserted into a degenerated disc region to provide support, and subsequently rehydrated so that it expands to provide rubber-like structural support so that proper disc height is regained. An implant 80 used in nucleoplasty preferably has an initial height $H_1$ at its largest dimension between about 3 mm and about 17 mm. Top and bottom surfaces 81a, 81b preferably may be radiused to approximate the concavity of the vertebral endplates, and preferably have a radius of between about 50 mm and about 70 mm. In one exemplary embodiment, top and bottom surfaces 81a, 81b are protruding and convex with a radius of about 60 mm.

Figure 14:
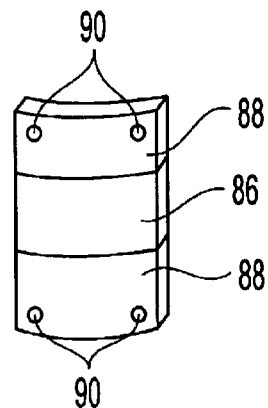
FIGS. 13–15 show ligament replacements using bone implants of the present invention.
Figure 13:
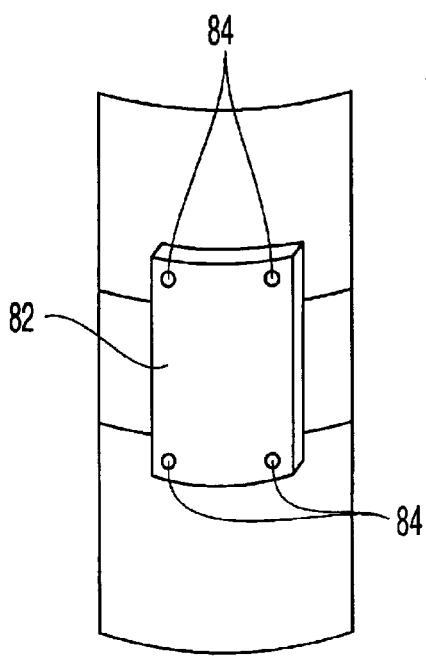
Figure 15:
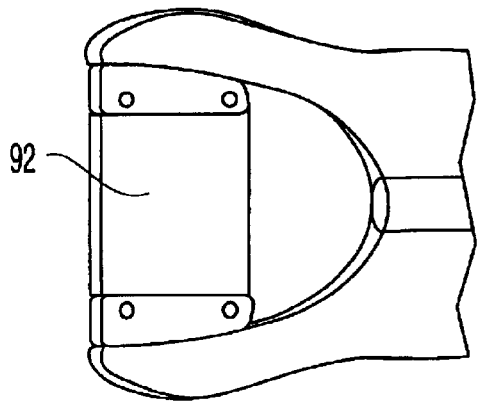

Referring to FIGS. 13–15, the use of demineralized and partially demineralized cortical bone in ligament replacements is shown. A demineralized cortical bone, generally rectangular plate 82 may be fastened in place using fasteners 84 located in corners of the plate. In other embodiments, alternate shapes of plate 82 may be used. The plate may be used, for example, to replace the anterior longitudinal ligament (ALL) that extends over the length of the lumbar spine anterior to the vertebral bodies, or the interspinous ligament (ISL) that attaches adjoining spinous processes and serves, for example, to limit forward bending. As shown for example in FIG. 14, partially demineralized cortical bone for use in ALL may include a demineralized section 86 bordered above and below by mineralized sections 88. The mineralized sections retain rigidity, and thus are most suitable for containing fastener holes 90. Referring to FIG. 15, a lateral view of the spine is shown with a partially demineralized cortical bone 92 used to replace an ISL disposed adjacent the spinous process.

Figure 16:
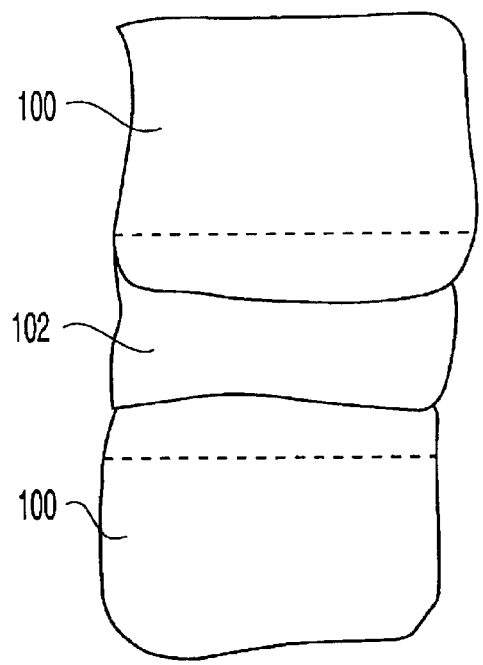
FIGS. 16–18 show the use of partially demineralized bone struts for disc replacement according to the present invention.
Figure 17:
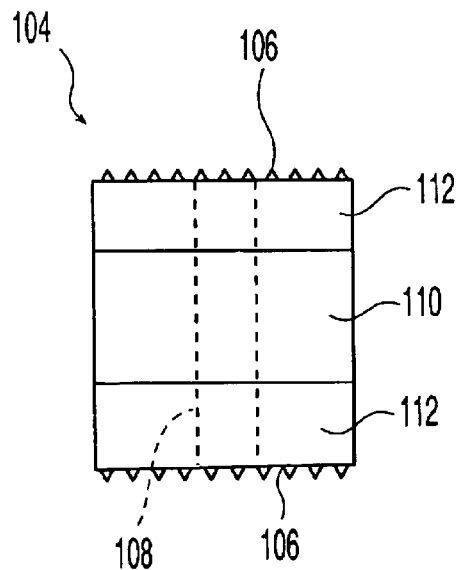
Figure 18:
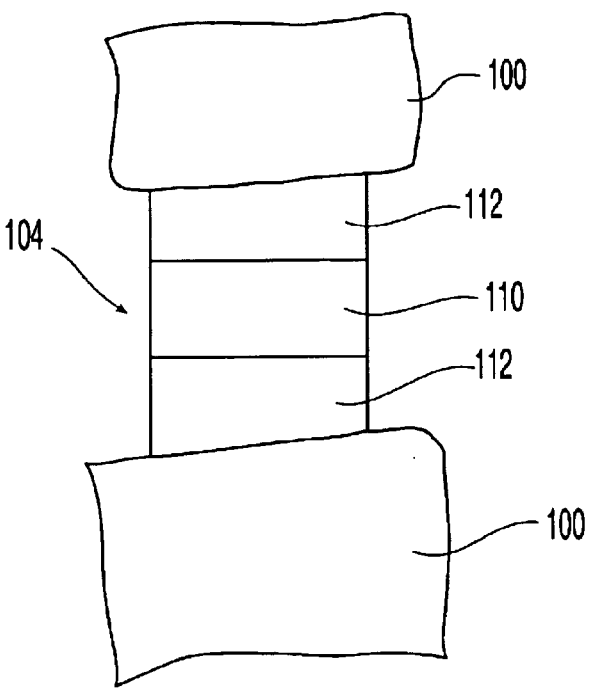

Turning to FIGS. 16–18, the use of demineralized or partially demineralized femoral struts for disc replacement is shown. The pertinent spinal structures are shown in FIG. 16, with a pair of vertebral bodies 100 disposed adjacent a disc 102. A generally cylindrical femoral strut 104 with teeth 106 and a central hole 108, includes a demineralized central portion 110 and mineralized portions 112. Once femoral strut 104 is implanted between vertebral bodies 100, mineralized portions 112 advantageously fuse with vertebral bodies 100, while demineralized central portion 110 mimics the behavior of disc-like collagen.

Figure 19:
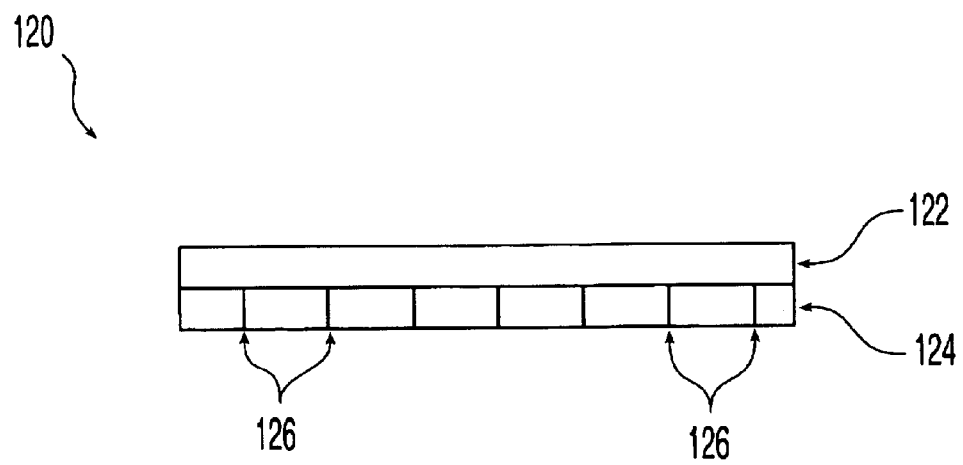
FIGS. 19–21 show a bendable implant of the present invention.
Figure 20:
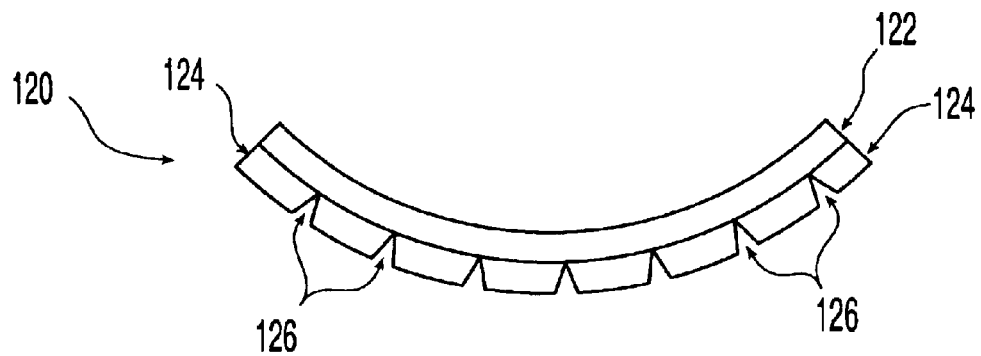
Figure 21:
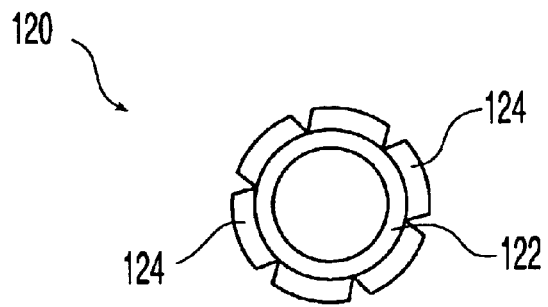

Another demineralized cortical bone implant 120 is shown in FIGS. 19–21. Implant 120 preferably includes a partially demineralized layer 122 and a mineralized, mechanically stronger layer 124. Slits 126 are cut in mineralized layer 124, and the pliability of layer 122 permits implant 120 to be bent as shown in FIGS. 20–21.

Figure 22:
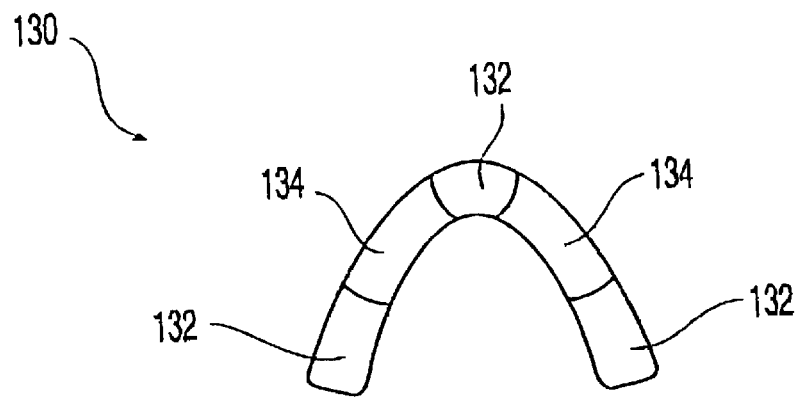
FIGS. 22–23 show bone cords of the present invention.
Figure 23:
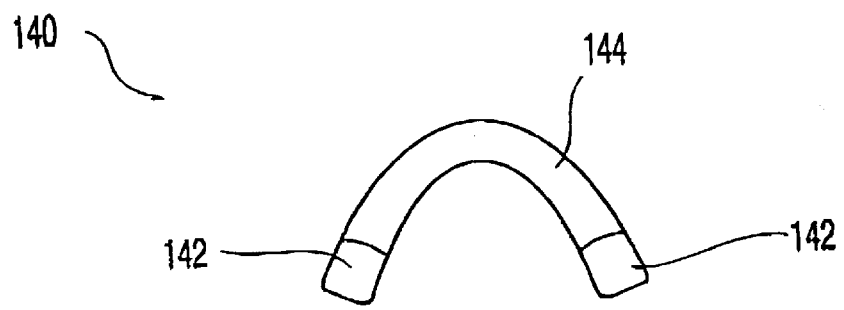

Referring to FIGS. 22–23, demineralized cortical bone may also be used in laminoplasty, the replacement of bone at the site of a previous excision in order to re-establish structural support and protection of the spinal cord. In laminectomy, the lamina and spinous process have been removed, while in laminotomy only a portion of the lamina is removed. A demineralized cortical bone cord 130 with mineralized cortical portions 132 and demineralized portions 134 to provide flexibility. Cord 130 may have free ends suitable for fixation, for example, to the exposed portions of the lamina following removal of a lamina section. Alternatively, a demineralized cortical bone cord 140 with mineralized cortical portions 142 and demineralized central portion 144 may similarly be used. Cords 130, 140 are used to bridge the gap created by the tissue excision. As discussed above with respect to other embodiments of the present invention, fastener holes may be located in the mineralized portions of the cortical bone cords.

Figure 24:
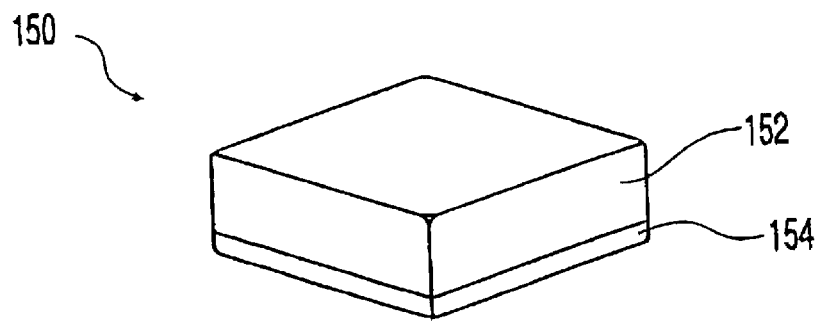
FIG. 24 shows a cortico-cancellous demineralized bone of the present invention.

Turning to FIG. 24, a section 150 of cortico-cancellous demineralized bone taken, for example, from the wall where the transition from the midshaft to the condyle of a bone occurs. A layer of cancellous bone 152 and a layer of cortical bone 154 may be jointly demineralized, resulting in a bone implant with two types of properties. Such selectively demineralized bone is particularly useful in maxillofacial procedures including reconstructive procedures as well as elective procedures such as face lifts, chin augmentations, cheek enhancements, and eye brow lifts. The demineralized region is relatively soft, while the mineralized region remains relatively hard and thus better accommodates implant fixation screws.

Figure 25:
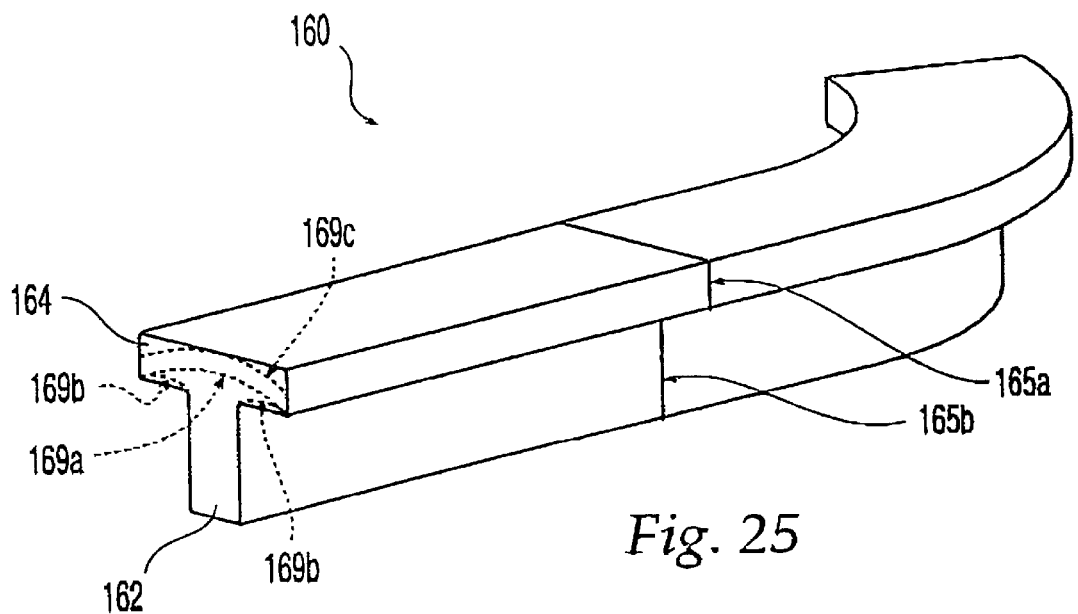
FIGS. 25–27 show cranial flap void and burr hole filling according to the present invention.
Figure 26:
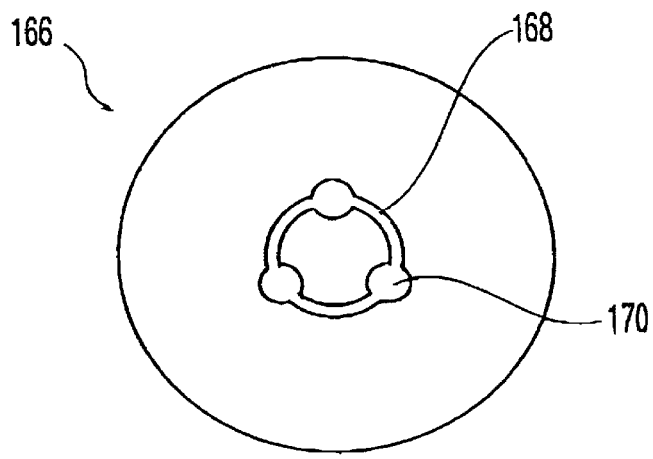
Figure 27:
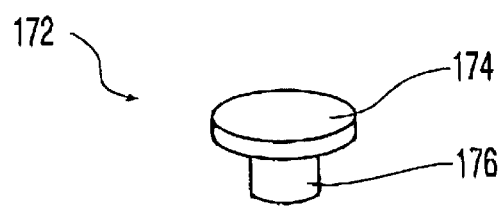

As shown in FIGS. 25–27, demineralized bone also can be used as a cranial flap void filler. In particular, during craniotomies, which are surgical procedures performed in the treatment of various brain problems such as tumors, aneurysms, blood clots, head injuries, abscesses, and the like, access to the brain is achieved by the creation of a hole in the bone that defines the skull. The hole or "window" in the skull is usually created by identifying the area of the brain to which access is needed, drilling several holes into the skull near the periphery of this area, inserting a cutting tool into one of the holes, and making cuts from one hole to another. Removal of the cut-out area of the skull, generally referred to as a bone flap, allows the desired access to the brain. After the desired medical or surgical procedure on the brain has been performed, the bone flap must be replaced and held in a stable position to allow the skull to heal.

Typically, when the bone flap is replaced in the region from which it was removed, gaps or voids remain between the bone flap and skull due to the cutting operation. To fill the gaps or voids, pliable, demineralized cortical bone may be used. For example, pliable, demineralized cortical bone may be inserted in the void 168 formed in the cranial region 166 of the skull. In one preferred embodiment, a generally T-shaped bone implant 160 is inserted in void 168 so that first portion 162 fits in void 168, while second portion 164 abuts the top of cranial region 166 of the skull. Preferably, first portion 162 of bone implant 160 is demineralized to provide flexibility, while second portion 164 remains mineralized bone to provide stiffness. To provide flexibility, slits 165a may extend through parts of second portion 164. Similarly, slits 165b may extend through a part of first portion 162, and may be aligned with slits 165a. In one exemplary embodiment, implant 160 is provided with an upper side 169a of second portion 164 that may be arcuate in cross-section and preferably concave. In another exemplary embodiment, second portion 164 is provided with lower arcuate portions 169b that generally match the contour of the skull in the region of use. An arcuate, upper portion 169c also may be provided. Such a flexible implant 160 thus permits the filling of a curved channel such as a void 168. In an alternate embodiment, demineralized cancellous bone may be used.

Burr holes 170 may be filled with covers formed of fully or partially demineralized bone as well. A burr hole cap 172 is shown in FIG. 27, with an upper portion 174 and a lower portion 176. Burr hole cap 172 may be formed of cortico-cancellous bone, with a cortical upper portion 174 and a lower cancellous portion 176. In addition, a portion of cap 172 may be demineralized, such as upper portion 174, while another portion such as lower portion 176 may be mineralized.

The "memory" properties of demineralized cancellous bone, as discussed above, may also be used to provide selectively compressible portions of a bone implant such as T-shaped bone implant 160 or burr hole cap 172. For example, in one preferred embodiment, lower portion 176 of cap 172 is demineralized cancellous bone, while upper portion 174 is mineralized or demineralized cortical bone. The demineralized cancellous bone of lower portion 176 may be hydrated so that it assumes a soft state in which it may be compressed to a smaller configuration, and then subsequently allowed to dry and harden in the compressed state. After insertion of the compressed lower portion 176 into a burr hole 170, lower portion 176 may be rehydrated and permitted to expand back to its original shape, regaining soft, spongy properties, and filling burr hole 170.

In an alternate embodiment of T-shaped bone implant 160, first portion 162 is formed of demineralized cancellous bone and fits in void 168, while second portion 164 is formed of cortical bone and is disposed proximate the top of cranial region 166 of the skull. Thus, the aforementioned "memory" properties of demineralized cancellous bone may be used to provide a desired fit of T-shaped bone implant 160 in void 168.

In yet another alternate embodiment, T-shaped bone implant 160 and one or more burr hole caps 172 may be provided as a unitary structure. The variable dimensions of the void 168 and burr holes 170 may be accommodated by the expandable "memory" properties of the demineralized cancellous bone portion.

Figure 28:
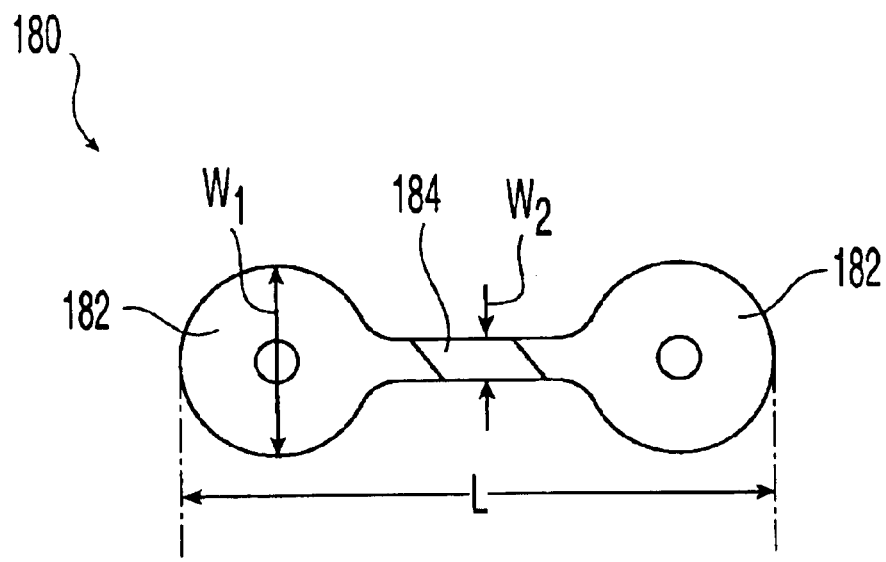
FIGS. 28–29 show dogbone-shaped plates of the present invention.
Figure 29:
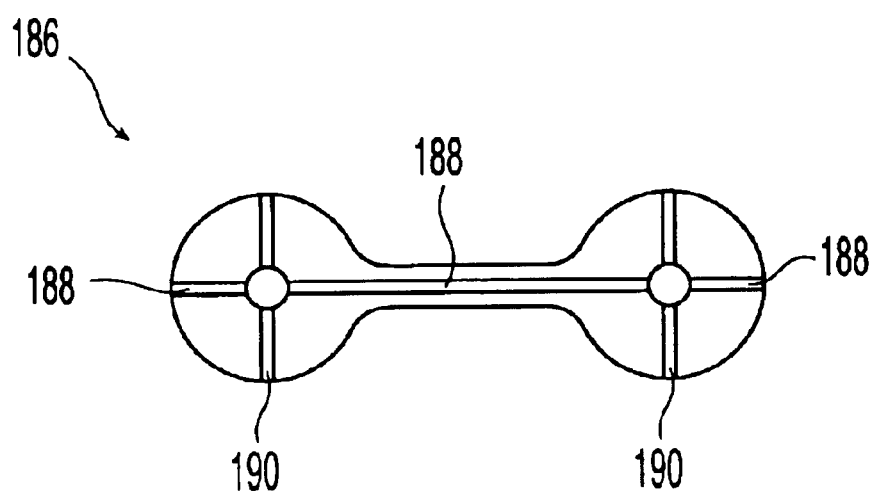

Turning to FIGS. 28–29, additional embodiments of implants produced from partially demineralized cortical bone are shown. Preferably, dogbone-shaped or dumbbell-shaped plates 180, 186 are formed of a unitary body with a pair of generally symmetrical side portions having a first width $W_1$, and a central portion disposed therebetween having a second width $W_2$ which is less than the first width. Plate 180 includes mineralized portions 182 and demineralized portion 184. Portion 184 is disposed diagonally across plate 180 to facilitate movement. In the embodiment of plate 186, demineralized portions 188, 190, which may be perpendicular or otherwise transversely disposed with respect to each other, permit angulation of plate 186 with more than one degree of freedom. Such dogbone plates may be used, for example, in thin areas of the face where fixation is required. In one embodiment, plates 180, 186 may have, for example, an overall length of between about 10 mm and about 20 mm, as measured for example along the central longitudinal axis defined by demineralized portion 188 of plate 186. In addition, plates 180, 186 preferably may have, for example, a maximum width $W_1$ between about 4 mm and about 7 mm, as measured for example along the axis defined by demineralized portion 190 of plate 186, and may have, for example, a thickness between about 1 mm and about 3 mm. In one exemplary embodiment, a dogbone-shaped plate 180, 186 has a length of about 15 mm, a maximum width of about 5 mm, and a thickness of about 2 mm.

Figure 30:
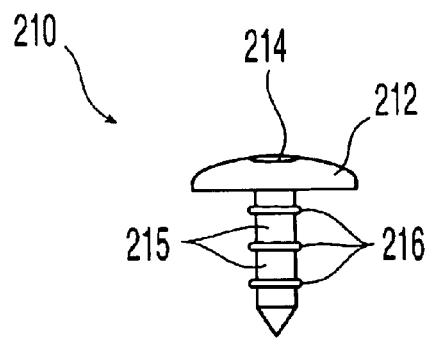
FIG. 30 shows a cortical tack or suture anchor of the present invention.

Referring to FIG. 30, a cortical tack or suture anchor 210 is shown, including a head 212, eyelet 214, and shaft 215 with ribs 216. All areas of suture anchor 210 except ribs 216 maybe masked and thereafter subjected to a demineralizing agent. Following treatment, head 212 remains hard, while demineralized ribs 216 are malleable. Once inserted into a hole in bone, the demineralized ribs 216 of suture anchor 210 permit an interference fit, and may serve as resilient o-rings. Thus, when a suture anchor 210 is pressed into a hole, the demineralized o-ring structure provides holding power to resist removal or backout of the suture anchor from the hole.

Figure 31:
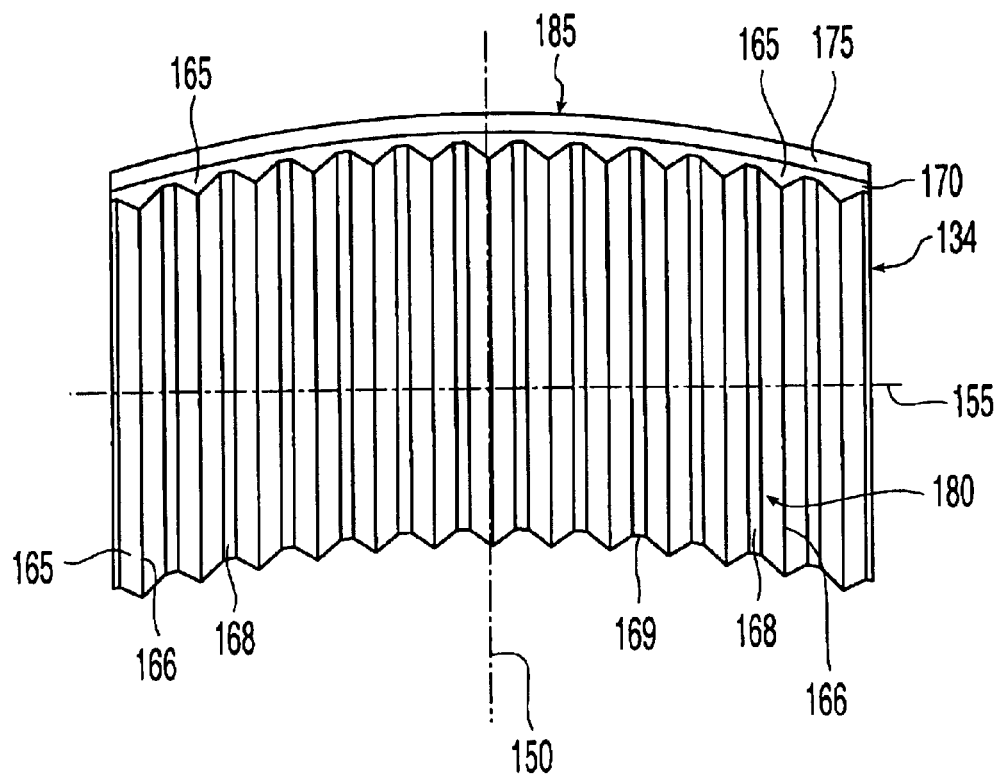
FIG. 31 shows an embodiment of a ribbed bone sheet.

In FIG. 31 an implantable bone sheet 134 that exhibits selective directional properties is disclosed. Bone sheet 134 may be formed of mineralized or demineralized bone, and may be produced from, and in a manner similar to, cylindrical tube or shell 16 of FIGS. 1 and 2. Sheet 134 has a longitudinal axis 150 and a cross axis 155 perpendicular to longitudinal axis 150. A plurality of corrugations or ribs 165 extend along the length L of the sheet 134 parallel to longitudinal axis 150. The ribs 150 provide a greater thickness and stiffness to the sheet. In particular the ribs resist bending in the direction along which they extend while providing greater flexibility in the opposite direction. The sheet is more flexible in the direction opposite the direction of the ribs and may be formed into a tube similar to that shown in FIGS. 2 and 8 (but with the ribs, although the perforations may or may not be included).

The ribs may be of any shape, for example, square or triangle cross-section. As shown in FIG. 31, the ribs may be formed having pointed or rounded peaks 166 and may form troughs 168 therebetween. The troughs 168 may have a flat section 169 which separates adjacent ribs 165. Instead of ribs 134, projections such as, for example, teeth may be used. By varying the thickness, height, shape, number and direction of the ribs 165 or projections, the sheet 134 can be tailor designed to have the desired properties in the desired directions.

The sheet 134 may be formed to have a mineralized bone section 170 and demineralized section 175. The demineralized section provides flexibility to the sheet while the mineralized section provides stiffness. Alternatively, the sheet 134 may be formed by machining a bone section, whether it be in the form of a sheet or precursor tube, to have the ribs or other projections and then subjecting the sheet or tube to demineralization agents. The sheet or tube may be subjected to demineralization from one or both sides. Where the sheet or tube is subject to demineralization agents from side 185, the sheet may take the form shown in FIG. 31 where it has a demineralized section 175 and a mineralized section 170. The demineralizing agents also may attack only the side 180, having the ribs as shown in FIG. 31, in which case because of the greater thickness at the ribs, the demineralized section of the sheet will take a shape that conforms more closely to the outer configuration of the ribbed side of the sheet. In other words, the interface between the demineralized section and the mineralized section may not have the straight planar configuration as shown in FIG. 31 but instead will approximate the shape of the ribs.

If the demineralizing agent were applied to both sides of the sheet or tube, the resulting sheet may have an interior mineralized section which corresponds roughly to the ribs because of the greater thickness of the sheet where the ribs are located. Depending upon the time with which the demineralizing agent is applied to the bone section, the thickness of the mineralized section can be varied. If the mineralized agents were applied to both sides for a sufficient amount, the resulting sheet or tube may have a plurality of interior discrete mineralized sections between and dispersed in the field of demineralized bone. As a result of the ribs or projections which provide a greater localized thickness, a mineralized section may remain while its surrounding areas where the sheet may be less thick has no mineralized bone remaining. The ribs or projections are configured to provide the desired flexibility in the desired direction while retaining the desired stiffness in the desired direction. The sheet 134 is preferably formed of cortical bone and the grain of bone material may extend in the same or a different direction than the ribs 165.

The side 185 may be substantially smooth, or may have ribs as illustrated for side 180 in FIG. 31, or other projections. Side 185 may have a ribbed design similar to or different than side 180. For example, the ribs on side 185 may extend in the same direction as side 180 or may extend in a direction transverse or orthagonal to the ribs of side 180. It will be appreciated that while FIG. 31 has been illustrated with ribs, the sheet may alternatively have projections such as teeth on one or both sides. The sheet also may be provided with perforations or be subject to masking selective areas as illustrated in FIGS. 1–4.

As discussed herein, demineralized cortical, cancellous, and cortico-cancellous bone may be used as a relatively soft substance for enhancing anatomical areas such as during plastic surgery, or for filling defect regions resulting from disease, congenital conditions, or surgical procedures. Demineralized bone of the present invention may also be formed into screws, which advantageously are less brittle than screws formed of mineralized bone. In particular, selective demineralization may be undertaken for portions of a screw structure so that a surgeon applying the screw receives tactile feedback from the pliable, demineralized portion when certain stress is reached. Angulation control also is possible by selectively demineralizing the screw.

Other processes of the present invention include the recovery of the minerals removed from the demineralizing of the bones, and the reintroduction of these minerals into bone implants. In addition, the various machining operations for the production of bone implants produce different bone fibers, bone powder and particulates, bone chips, or combinations thereof. Milling of cortical bone can produce long and short fibers. The thickness and length of the fibers is a function of the blade design, milling speed of the milling operation, and the feed rate of the bone. Grinding can produce powder or particulates of varying sizes, which may be sieved to separate the powder or particulates into desired size ranges. Moreover, bone chips may be produced by a lathe operation. The properties and usage of these by-products vary depending upon the degree of any demineralization. For example, cortical long fibers produced by milling of bone may be treated in hydrochloric acid for an extended period of time, and allowed to demineralize to a mushy consistency. The demineralized long fibers tend to clump together. Additional pressing means may be used to further encourage clumping. Demineralized cortical fibers may be pressed together in a wet or semi-wet state in a compression molding operation to produce a part of a desired geometry. Once dry, the solid part has significant strength.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. For example, a demineralized cortical shell may be sized to behave like a rubber band, and used for a similar purpose. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A plate comprising:
   a unitary body with a pair of portions each having a first width and a central portion disposed therebetween having a second width, the first width being substantially greater than the second width, and the body being formed of cortical bone; and
   the unitary body further having at least one partially demineralized region with a third width smaller than the second width,
   wherein the at least one partially demineralized region confers flexibility to the plate.

2. The plate of claim 1, further comprising a plurality of faster holes in the unitary body.

3. The plate of claim 2, wherein the body has a central longitudinal axis, and the at least one partially demineralized region comprises a first at least partially demineralized region that is coaxial with the longitudinal axis.

4. The plate of claim 3, wherein the first at least partially demineralized region extends substantially across the unitary body.

5. The plate of claim 3, wherein the fastener holes are disposed proximate ends of the body.

6. The plate of claim 5, wherein the fastener holes are disposed on a central longitudinal axis, and the first at least partially demineralized region is coaxial therewith.

7. The plate of claim 6, wherein the at least one partially demineralized region further comprises at least a second at least partially demineralized region that is disposed transverse to the first at least partially demineralized region.

8. The plate of claim 7, wherein the at least second at least partially demineralized region is generally perpendicular to the first at least partially demineralized region.

9. The plate of claim 8, wherein the at least second at least partially demineralized region intersects at least one fastener hole.

10. The plate of claim 1, wherein the body is relatively thin compared to each of the first widths and the second width.

11. The plate of claim 10, wherein the body has a central longitudinal axis and the at least partially demineralized region extends transverse to the central longitudinal axis.

12. The plate of claim 11, further comprising a plurality of fastener holes in the unitary body.

13. The plate of claim 1, wherein the body has a central longitudinal axis, and the length of the body along the central axis is between about 10 mm and about 20 mm.

14. The plate of claim 13, wherein the first width is between about 4 mm and about 7 mm.

15. The plate of claim 14, wherein the body has a thickness between about 1 mm and about 3 mm.

16. The plate of claim 14, wherein the first width is about 5 mm, and the body has a length of about 15 mm, along the central longitudinal axis and a thickness of about 2 mm transverse to the central longitudinal axis.

* * * * *